(12) United States Patent
Sadohara et al.

(10) Patent No.: US 8,616,698 B2
(45) Date of Patent: Dec. 31, 2013

(54) METHOD FOR EVALUATING PIGMENT INK FOR INK-JET RECORDING AND METHOD FOR PRODUCING PIGMENT INK FOR INK-JET RECORDING

(75) Inventors: Hitomi Sadohara, Nagoya (JP); Hiromitsu Sago, Tokai (JP); Yuko Iwamura, Nagoya (JP); Akiko Miyajima, Aichi-ken (JP)

(73) Assignee: Brother Kogyo Kabushiki Kaisha, Nagoya-shi, Aichi-ken (JP)

( * ) Notice: Subject to any disclaimer, the term of this patent is extended or adjusted under 35 U.S.C. 154(b) by 1147 days.

(21) Appl. No.: 12/556,982

(22) Filed: Sep. 10, 2009

(65) Prior Publication Data

US 2010/0058853 A1    Mar. 11, 2010

(30) Foreign Application Priority Data

Sep. 10, 2008 (JP) ................................. 2008-231877
Sep. 10, 2008 (JP) ................................. 2008-231878
Sep. 10, 2008 (JP) ................................. 2008-231879

(51) Int. Cl.
*B41J 2/01* (2006.01)
*B41J 2/015* (2006.01)

(52) U.S. Cl.
USPC ............................................. 347/103; 347/21

(58) Field of Classification Search
None
See application file for complete search history.

(56) References Cited

U.S. PATENT DOCUMENTS

| 5,609,671 | A | 3/1997 | Nagasawa |
| 5,837,045 | A | 11/1998 | Johnson et al. |
| 7,235,126 | B2 | 6/2007 | Tani et al. |
| 8,042,906 | B2 * | 10/2011 | Chiwata et al. ................. 347/21 |
| 2009/0079784 | A1 * | 3/2009 | Chiwata et al. ................. 347/21 |
| 2012/0105562 | A1 * | 5/2012 | Sekiguchi et al. ............ 347/103 |

FOREIGN PATENT DOCUMENTS

| JP | 08-003498 | 1/1996 |
| JP | 2000-513396 | 10/2000 |
| JP | 2003-128955 | 5/2003 |
| JP | 2004-277562 | 10/2004 |
| JP | 2005-008725 | 1/2005 |
| JP | 2006-008897 | 1/2006 |

* cited by examiner

*Primary Examiner* — Andre Allen
(74) *Attorney, Agent, or Firm* — Banner & Witcoff, Ltd.

(57) ABSTRACT

An evaluation method for evaluating a pigment ink for ink-jet recording used together with a dye ink and containing a pigment and water includes an aggregation property evaluation method for the pigment in which 10 parts by weight of an aqueous sodium chloride solution is added to 100 parts by weight of the pigment ink; the evaluation method including first aggregation property evaluation adding an X wt % aqueous sodium chloride solution; and second aggregation property evaluation adding a Y wt % aqueous sodium chloride solution; wherein concentrations of the aqueous sodium chloride solutions are set to fulfill the following condition in the first and second aggregation property evaluations: $1.0 \leq X < Y \leq 2.5$. The optical density of a printed matter and the dispersion stability of the pigment when the pigment ink is brought in contact with the dye ink can be easily evaluated before the printing.

15 Claims, 2 Drawing Sheets

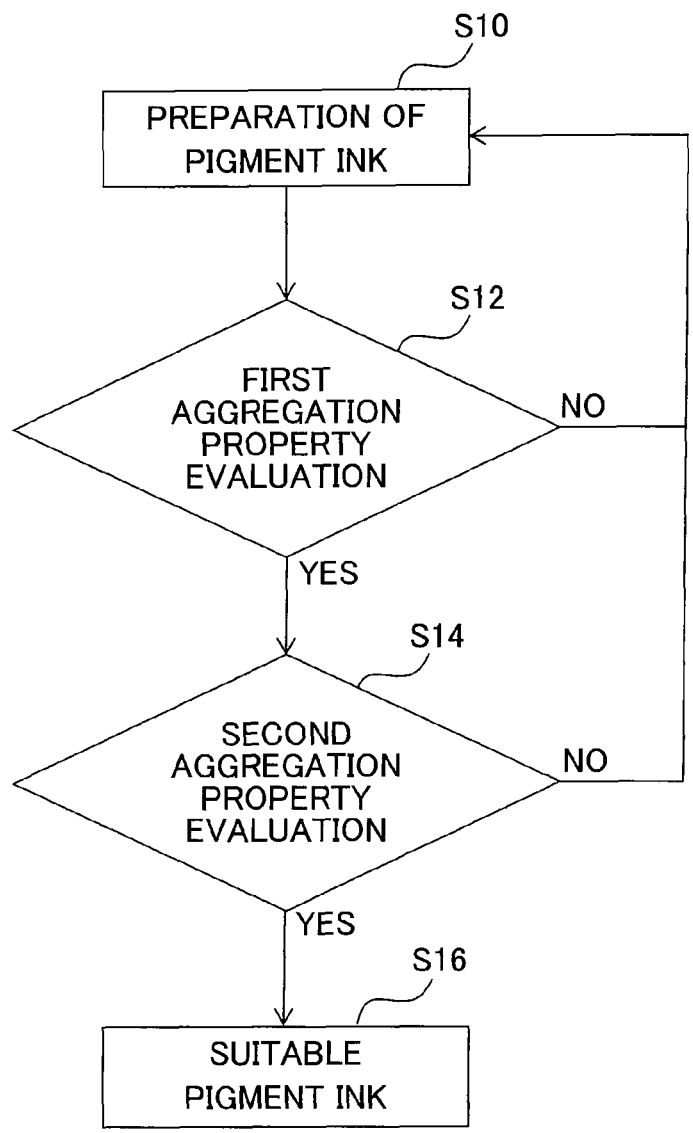

METHOD FOR EVALUATING PIGMENT INK FOR INK-JET RECORDING AND METHOD FOR PRODUCING PIGMENT INK FOR INK-JET RECORDING

CROSS REFERENCE TO RELATED APPLICATION

The present application claims priority from Japanese Patent Applications No. 2008-231879, filed on Sep. 10, 2008, No. 2008-231877, filed on Sep. 10, 2008, and No. 2008-231878, filed on Sep. 10, 2008, the disclosures of which are incorporated herein by reference in their entirety.

BACKGROUND OF THE INVENTION

1. Field of the Invention

The present invention relates to an evaluation method for evaluating a pigment ink for ink-jet recording and a production method for producing the pigment ink for ink-jet recording.

2. Description of the Related Art

A pigment ink for ink-jet recording, which contains a pigment and water, has been hitherto widely used. A printed matter, which is printed by using the pigment ink, is excellent in the weather resistance and the water resistance. However, the pigment ink involves such a problem that the pigment ink is difficult to be fixed on a recording medium such as a printing paper sheet, and that the optical density of the printed matter is low. Further, the pigment ink also involves such a problem that the pigment tends to aggregate or coagulate, and the pigment ink is inferior in the dispersion stability. The inferior dispersion stability of the pigment means that the storage stability of the pigment ink itself is low. The inventors of this invention recognize that, other than the problem associated with the storage stability of the pigment ink, the inferior dispersion stability of the pigment also causes the following problem. In a case that the pigment ink inferior in the dispersion stability is used, for example, in an ink set together with a dye ink, the pigment ink is brought in contact with the dye ink before the printing at an ink jetting surface of an ink jet recording head in some cases. This situation happens, for example, when the ink jetting surface is wiped with a wiper so as to perform cleaning for the ink jetting surface. When the pigment ink which is inferior in the dispersion stability as described above and the dye ink are brought in contact with each other on the ink jetting surface, the pigment ink is affected, for example, by the Na+ counter ion contained in the dye ink and thus the pigment ink is easily aggregated, thereby clogging a nozzle hole in the ink jetting surface. This problem is very serious in an ink-jet head having a construction in which a plurality of color inks are jetted from a single jetting surface.

In order to solve the above problem associated with the optical density, there is proposed a pigment ink in which a water-soluble resin is blended (Japanese Patent Application Laid-open No. 2004-277562 and No. 2005-8725). In this pigment ink, by blending the water-soluble resin, the aggregation of the pigment on the recording medium is enhanced and the optical density of the printed matter is increased.

Further, in order to increase the optical density of the printed matter and to increase the dispersion stability of the pigment, there is provided a pigment ink containing acrylic resin (Japanese Patent Application Laid-open No. 2006-8897).

However, in the pigment ink in which the water-soluble resin is blended, the dispersion stability is lowered because the aggregation of the pigment is enhanced. Therefore, in a case that this pigment ink is used together with a dye ink in an ink jet recording apparatus, the pigment aggregates when the dye ink is brought in contact with the pigment ink and the aggregated matter is adhered to the nozzle of the ink-jet head, which in turn causes the discharge failure or unsatisfactory failure as a result. Further, also in the pigment ink in which the acrylic resin is blended, the problem of the aggregation, caused by the contact of the pigment ink with the dye ink before the printing, has not been resolved. Namely, among the conventional pigment inks, there is not such a pigment ink with which the high optical density of the printer matter is realized and which is capable of preventing the discharge failure caused by the contact of the pigment ink with the dye ink before the printing.

Conventionally, the dispersion stability of the pigment and the optical density of the printed matter, which relate to the pigment ink as described above, have been generally evaluated by performing a storage stability test and a printing test. Such an evaluation method requires a long test time and a complicated operation.

A method has been suggested, in which the dispersion stability of the pigment and the optical density of the printed matter are evaluated by the aggregation value (coagulation value) of the pigment ink with respect to sodium chloride (Japanese Patent Application Laid-open No. 2006-8897).

However, the evaluation of the dispersion stability in the evaluation method based on the aggregation value is an evaluation of the dispersion stability of the pigment in the pigment ink. With the evaluation method based on the aggregation value, it is impossible to evaluate the dispersion stability of the pigment for a case that the pigment ink is used in an ink set together with the dye ink and when the pigment ink is brought in contact with a dye ink before the printing. Further, it is desired that a method is developed which is capable of effectively evaluating the dispersion stability of the pigment when the pigment ink is jetted onto a paper surface. In particular, the optical density of the printed matter is affected by the dispersion stability of the pigment

SUMMARY OF THE INVENTION

In view of the above, an object of the present invention is to provide an evaluation method for evaluating a pigment ink for ink jet recording wherein it is possible to easily evaluate, in a case that the pigment ink is used together with a dye ink, both of the optical density of a printed matter and the dispersion stability of the pigment when the pigment ink is brought in contact with the dye ink before the printing.

According to a first aspect of the present invention, there is provided an evaluation method for evaluating a pigment ink for ink jet recording which is used together with a dye ink for ink-jet recording and which contains a pigment and water, the method including:

performing an aggregation property evaluation method for the pigment in which 10 parts by weight of an aqueous sodium chloride solution is added to 100 parts by weight of the pigment ink, the aggregation property evaluation method for the pigment including:

performing first aggregation property evaluation in which the aqueous sodium chloride solution having an X % by weight concentration is added to the pigment ink; and performing second aggregation property evaluation in which the aqueous sodium chloride solution having a Y % by weight concentration is added to the pigment ink;

wherein the concentrations of the aqueous sodium chloride solutions are set to fulfill a following condition (A) in the first aggregation property evaluation and the second aggregation property evaluation:

$$1.0 \leq X < Y \leq 2.5. \tag{A}$$

According to a second aspect of the present invention, there is provided an evaluation method for evaluating a pigment ink for ink-jet recording which is used together with a dye ink for ink jet recording ink, the method including:

preparing pigment inks of various compositions, each of the pigment inks containing a pigment and water;

performing a first aggregation property evaluation, for evaluating aggregation property of the pigment for each of the pigment inks, in which 10 parts by weight of a 1.0 to 1.5% by weight aqueous sodium chloride solution is added to 100 parts by weight of the pigment ink; and performing a second aggregation property evaluation, for evaluating the aggregation property of the pigment for each of the pigment inks, in which 10 parts by weight of a 2.0 to 2.5% by weight aqueous sodium chloride solution is added to 100 parts by weight of the pigment ink; and selecting a pigment ink, among the pigment inks of various compositions, in which the pigment does not aggregate in the first aggregation property evaluation and the pigment aggregates in the second aggregation property evaluation.

According to the evaluation method for evaluating the pigment ink for ink-jet recording, it is possible to easily evaluate both of the optical density of a printed matter and the dispersion stability of the pigment when the pigment ink is brought in contact with a dye ink before the printing. Therefore, according to the evaluation method of the present invention, it is easy to investigate the composition of the pigment ink; and consequently, it is easy to develop a high performance pigment ink for ink jet recording, wherein the aggregation (coagulation), which would be otherwise caused by the contact with the dye ink before the printing, is avoided, and the optical density of the printed matter is high.

BRIEF DESCRIPTION OF THE DRAWINGS

FIG. 2 shows a flow chart showing a production process of a pigment ink according to the present invention.

DESCRIPTION OF THE PREFERRED EMBODIMENTS

Figure 1:
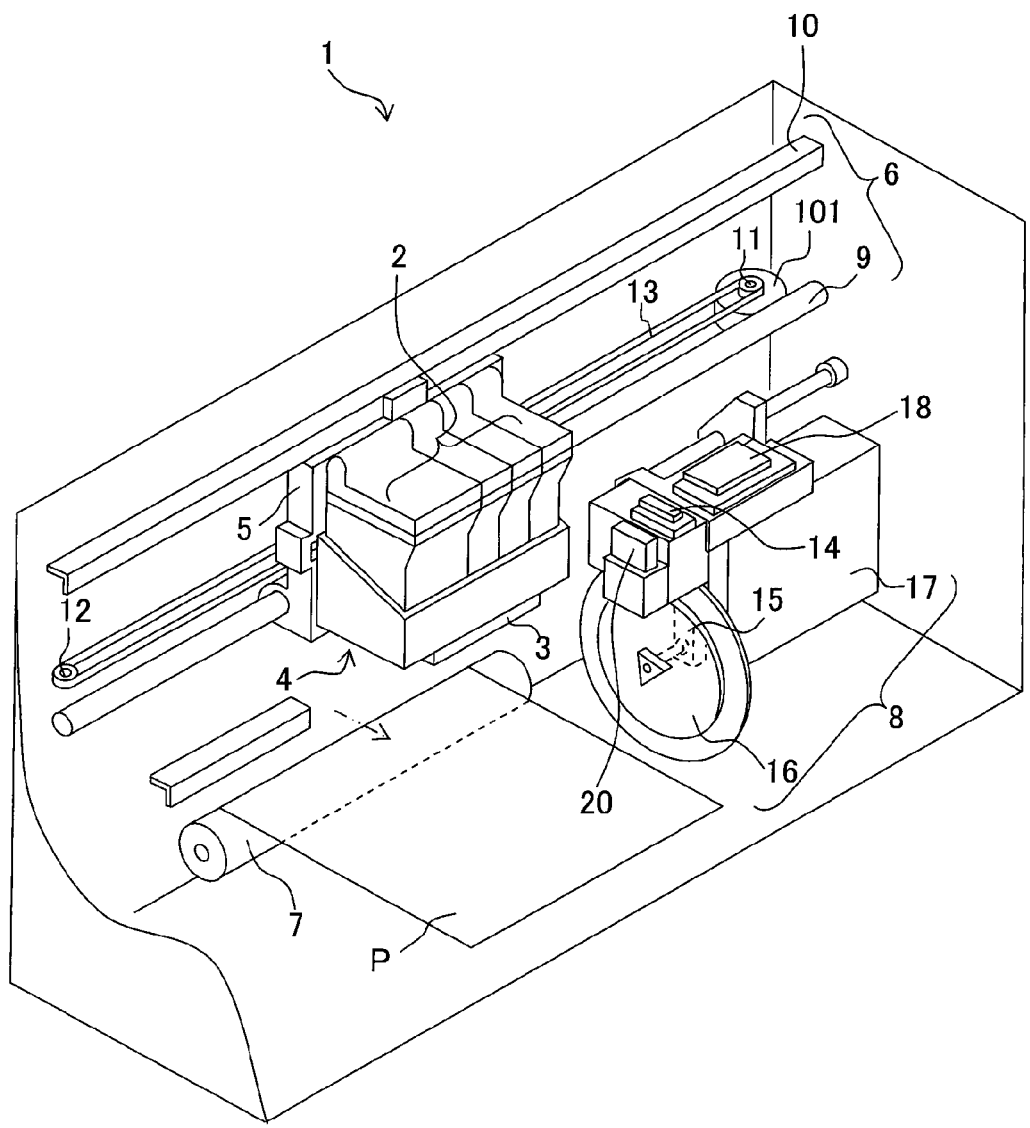
FIG. 1 shows a schematic perspective view illustrating an exemplary construction of an ink-jet recording apparatus.

In the evaluation method of the present invention, a dispersion state of the pigment is evaluated in the first aggregation property evaluation in a case that the pigment ink for ink-jet recording is brought in contact with a dye ink for ink-jet recording before printing; and an optical density of a printed matter is evaluated in the second aggregation property evaluation.

In the evaluation method of the present invention, dispersion stability of the pigment, when (to be provided when) the pigment ink for ink-jet recording is brought in contact with a dye ink for ink jet recording before printing, is judged to be good if dispersion of the pigment is maintained in the first aggregation property evaluation; and an optical density of a printed matter is judged to be good if the pigment aggregates in the second aggregation property evaluation. The case or situation, in which the dispersion of the pigment is maintained as described above, refers to such a situation that the pigment does not aggregate in the first aggregation property evaluation as will be described in Examples later on. The situation, in which the pigment aggregates, refers to such a situation that the pigment aggregates in the second aggregation property evaluation as will be described in Examples later on.

Next, the evaluation method for evaluating the pigment ink for ink-jet recording of the present invention will be explained in detail. As described above, the evaluation method of the present invention includes the first aggregation property evaluation and the second aggregation property evaluation.

As described above, in the evaluation method of the present invention, the X % by weight aqueous sodium chloride solution is added in the first aggregation property evaluation, and the Y % by weight aqueous sodium chloride solution is added in the second aggregation property evaluation. The concentrations of the aqueous sodium chloride solutions are set to fulfill the condition (A) described above in the first aggregation property evaluation and the second aggregation property evaluation. That is, the maximum value of the difference (Y–X) between X and Y is 1.5. The difference (Y–X) is preferably 1.0 and more preferably 0.5. X is preferably 1.0 and more preferably 1.5. Y is preferably 2.5 and more preferably 2.0.

In the evaluation method of the present invention, the pigment ink, for which the dispersion of the pigment is maintained in the first aggregation property evaluation, is judged to be such a pigment ink that the dispersion stability of the pigment is good or satisfactory when the pigment ink is brought in contact with the dye ink before the printing, and the discharge failure or the undischarge, which would be otherwise caused by the aggregation of the pigment, is not caused. This is based on the following hypothesis and experiment. The dye ink contains the counter ion of the dye such as sodium ion Na+; and the counter ion inhibits the dispersion stability of the pigment, thereby causing the pigment to aggregate. As described above, when the pigment and dye inks are brought in contact with each other due to the wiping of the ink-jet head, the pigment is thus caused to aggregate, which in turn leads to the clog-up of the nozzle. In the first aggregation property evaluation, by using the aqueous sodium chloride solution so as to evaluate the pigment aggregation brought about when the pigment ink is brought in contact with the sodium chloride, it is possible to grasp the situation that the pigment aggregates when the pigment ink is actually brought in contact with the dye ink. The inventors found out, through the experiments of the examples (which will be described later on), that there is a correlation between the concentration of the sodium chloride and the aggregation of the pigment ink brought about when the pigment ink is brought in contact with the dye ink. With this finding, it is possible to consider that if in a pigment ink the dispersion of the pigment is maintained in the first aggregation property evaluation, then such a pigment ink would not cause the discharge failure (unsatisfactory discharge) or the undischarge, as described above which would be otherwise caused due to the aggregation of the pigment, even when the pigment ink is used in combination (together with) the dye ink.

In the evaluation method of the present invention, the pigment ink, in which the pigment aggregates in the second aggregation property evaluation, is judged to be such a pigment ink that the optical density of the printed matter is high. This is based on the following hypothesis and experiment. The inorganic salt, which includes, for example, sodium chloride and calcium carbonate, is contained in the recording medium such as the printing paper sheet or the like. Therefore, when the pigment ink is landed on a surface of the recording medium, then sodium chloride or the like, which has a high solubility in water, is quickly dissolved in the pigment ink, and the pigment immediately aggregates. Accordingly, the optical density of the printed matter using the pigment ink is heightened. In the second aggregation property evaluation, by using the aqueous sodium chloride solution so as to evaluate the pigment aggregation brought about when the pigment ink is brought in contact with the sodium chloride, it is possible to grasp the situation that the pigment aggregates when the pigment ink is actually landed on the recording medium (paper). The inventors found out, through the experiments of the examples (which will be described later on), that there is a clear correlation between the concentration of the sodium chloride and the aggregation of the pigment ink brought about when the pigment ink is landed on the paper. Based on this finding, it is possible to consider that if a pigment ink satisfies the criterion for the second aggregation property evaluation, then with such a pigment ink the optical density of the printed matter would be sufficiently high after the printing.

Through the examples (to be described later on), it is found out that the concentration of the sodium chloride which indicates the aggregation of the pigment when the pigment ink lands on the paper (the evaluation standard concentration of the sodium chloride in the second aggregation property evaluation), is different from the concentration of the sodium chloride, which indicates the aggregation of the pigment when the pigment ink is brought in contact with the dye ink (the evaluation standard concentration of the sodium chloride in the first aggregation property evaluation). Namely, it is possible to evaluate, with the first aggregation property evaluation, the dispersion stability of the pigment which is brought about in a case that the pigment ink is brought in contact with the dye ink before the printing, by using the sodium chloride having a predetermined concentration; and it is possible to evaluate, with the second aggregation property evaluation, the aggregation of the pigment which is brought about when the pigment ink lands on the paper and to evaluate the increase in the optical density in the printed matter caused as a result of the pigment aggregation, by using the sodium chloride having a concentration which is different from the concentration of the sodium chloride used in the first aggregation property evaluation. Thus, in a case that the pigment ink is used together with the dye ink, it is possible to evaluate individually or separately the aggregations of the pigment ink which would occur before and after the printing respectively. Therefore, by using the first aggregation property evaluation and the second aggregation property evaluation in combination, there is provided a total evaluation method for the pigment ink in which the actual printing situation is appropriately reflected; and by using the total evaluation method, it has been possible to successively produce a pigment ink capable of preventing the clog-up of the nozzle before the printing and capable of obtaining a printer matter having a high optical density after the printing.

In the evaluation method of the present invention, the pigment ink as the evaluation objective contains the pigment and water.

The pigment is not limited; and those usable include, for example, carbon black, inorganic pigments, and organic pigments. The carbon black includes, for example, furnace black, lamp black, acetylene black, and channel black. The inorganic pigment includes, for example, titanium oxide, those based on iron oxide, and those based on carbon black. The organic pigment includes, for example, azo-pigments such as azo lake, insoluble azo-pigment, condensed azo-pigment, chelate azo-pigment and the like; polycyclic pigments such as phthalocyanine pigment, perylene and perynon pigments, anthraquinone pigment, quinacridone pigment, dioxadine pigment, thioindigo pigment, isoindolinone pigment, quinophthalone pigment and the like; dye lake pigments such as basic dye type lake pigment, acid dye type lake pigment and the like; nitro pigments; nitroso pigments; and aniline black daylight fluorescent pigment. Any other pigment is also usable provided that the pigment is dispersible in the water phase. The pigments as described above include, for example, C. I. Pigment Blacks 1, 6, and 7; C. I. Pigment Yellows 1, 2, 3, 12, 13, 14, 15, 16, 17, 55, 73, 74, 75, 83, 93, 94, 95, 97, 98, 114, 128, 129, 138, 150, 151, 154, 180, 185, and 194; C. I. Pigment Oranges 31 and 43; C. I. Pigment Reds 2, 3, 5, 6, 7, 12, 15, 16, 48, 48:1, 53:1, 57, 57:1, 112, 122, 123, 139, 144, 146, 149, 166, 168, 175, 176, 177, 178, 184, 185, 190, 202, 221, 222, 224, and 238; C. I. Pigment Violet 196; C. I. Pigment Blues 1, 2, 3, 15, 15:1, 15:2, 15:3, 15:4, 16, 22, and 60; and C. I. Pigment Greens 7 and 36.

The pigment may include self-dispersible pigments. The self-dispersible pigment is dispersible in water, without using any dispersing agent, for example, owing to the fact that at least one of the hydrophilic functional group and the salt thereof including, for example, carboxyl group, carbonyl group, hydroxyl group, and sulfon group is introduced into the surfaces of the pigment particles by the chemical bond directly or with any polyvalent group intervening therebetween.

The self-dispersible pigment is not limited. It is possible to use self-dispersible pigments subjected to the surface treatment by any one of methods described, for example, in Japanese Patent Application Laid-open No. 8-3498 and Published Japanese Translation of PCT International Publication for Patent Application No. 2000-513396. For example, any commercially available product may be used for the self-dispersible pigment. The commercially available product includes, for example, "CAB-O-JET (trade name) 200, 250, 260, 300, and 700" produced by Cabot Specialty Chemicals, "BONJET (trade name) BLACK CW-1, CW-2, and CW-3" produced by Orient Chemical Industries, Ltd., and "LIOJET (trade name) WD BLACK 002C" produced by Toyo Ink Mfg. Co., Ltd.

The pigment, which is usable as the raw material for the self-dispersible pigment, is not limited. It is possible to use any one of inorganic pigments and organic pigments. The pigment, which is suitable to perform the surface treatment, includes, for example, carbon blacks such as "MA8 and 100" produced by Mitsubishi Chemical Corporation and "Color Black FW200" produced by Degussa.

In the evaluation method of the present invention, the pigment ink as the evaluation objective may contain only one type of the pigment as described above, or the pigment ink may contain two or more types of the pigments.

The water is preferably ion-exchanged water or pure water (purified water). In the evaluation method of the present invention, the blending ratio (water ratio) of water with respect to the entire pigment ink as the evaluation objective is appropriately determined depending on, for example, the desired ink characteristics. The water ratio may be, for example, the balance of the other components.

In the evaluation method of the present invention, it is preferable that the pigment ink as the evaluation objective further contains a water-soluble organic solvent. The water-soluble organic solvent is classified, for example, into the moistening agent which prevents the ink from being dried at an end portion (forward end portion) of the ink-jet head and the permeating agent which adjusts the drying velocity on the recording paper surface.

The moistening agent is not limited, and includes, for example, lower alcohols such as methyl alcohol, ethyl alcohol, n-propyl alcohol, isopropyl alcohol, n-butyl alcohol, sec-butyl alcohol, and tert-butyl alcohol; amides such as dimethylformamide and dimethylacetamide; ketones such as acetone; ketoalcohols (ketone alcohols) such as diacetone alcohol; ethers such as tetrahydrofuran and dioxane; polyvalent alcohols such as polyalkylene glycols, alkylene glycols, and glycerol; 2-pyrrolidone; N-methyl-2-pyrrolidone; and 1,3-dimethyl-2-imidazolidinone. The polyalkylene glycol is not limited, and includes, for example, polyethylene glycol and polypropylene glycol. The alkylene glycol is not limited, and includes, for example, ethylene glycol, propylene glycol, butylenes glycol, diethylene glycol, triethylene glycol, dipropylene glycol, tripropylene glycol, thiodiglycol, and hexylene glycol. In particular, it is preferable to use polyvalent alcohols such as alkylene glycol and glycerol. In the evaluation method of the present invention, the pigment ink as the evaluation objective may contain only one type of the moistening agent as described above, or the pigment ink may contain two or more types of the moistening agents.

In the evaluation method of the present invention, the blending ratio (moistening agent ratio) of the moistening agent with respect to the entire pigment ink as the evaluation objective is not specifically limited. The blending ratio (moistening agent ratio) is, for example, 0% by weight to 95% by weight, preferably 5% by weight to 80% by weight, and more preferably 5% by weight to 50% by weight.

The permeating agent is not limited, and includes, for example, glycol ether compound. The glycol ether compound is not limited, and includes, for example, ethylene glycol methyl ether, ethylene glycol ethyl ether, ethylene glycol propyl ether, diethylene glycol methyl ether, diethylene glycol ethyl ether, diethylene glycol propyl ether, diethylene glycol butyl ether, triethylene glycol methyl ether, triethylene glycol ethyl ether, triethylene glycol propyl ether, triethylene glycol butyl ether, propylene glycol methyl ether, propylene glycol ethyl ether, propylene glycol propyl ether, propylene glycol butyl ether, dipropylene glycol methyl ether, dipropylene glycol ethyl ether, dipropylene glycol propyl ether, dipropylene glycol butyl ether, tripropylene glycol methyl ether, tripropylene glycol ethyl ether, tripropylene glycol propyl ether, and tripropylene glycol butyl ether. In the evaluation method of the present invention, the pigment ink as the evaluation objective may contain only one type of the permeating agent, or the pigment ink may contain two or more of the permeating agents.

In the evaluation method of the present invention, the blending ratio (permeating agent ratio) of the permeating agent with respect to the entire pigment ink as the evaluation objective is not specifically limited. The blending ratio (permeating agent ratio) is, for example, 0% by weight to 20% by weight. When the permeating agent ratio is in the range described above, it is possible to obtain more preferred permeability of the pigment ink into the paper. The permeating agent ratio is preferably 0.1% by weight to 15% by weight and more preferably 0.5% by weight to 10% by weight.

In the evaluation method of the present invention, the pigment ink as the evaluation objective may further contain a water-soluble resin. By adding the water-soluble resin to the pigment ink, it is possible to accelerate the aggregation of the pigment on the recording medium such as the printing paper, and it is possible to heighten the optical density of the printed matter. This is owing to the following effect of the water-soluble resin. It is known that the water-soluble resin is used as a dispersing agent for the pigment. Since the water-soluble resin has the hydrophilic group such as carboxyl group on the surface of the water-soluble resin, the water-soluble resin surrounds the pigment through the affinity with the group such as sulfate group introduced to the surface of the pigment by the surface treatment. At this time, since the water-soluble resin is also hydrated via the hydrophilic group with the water in the pigment ink, the water-soluble resin is stable in the pigment ink. However, when the pigment ink is jetted onto the paper and the water in the pigment ink is lost rapidly, the concentration of water-soluble resin becomes high, and thus the hydration effect in the pigment ink is lost. As a result, the water-soluble resin becomes unstable in the pigment ink, thereby causing the aggregation of the pigment. As the concentration of the water-soluble resin in the pigment ink is higher, this aggregation effect is more easily occurred. As the molecular weight of the water-soluble resin is greater, this aggregation effect is more easily occurred. Note that, however, if the molecular weight of the water-soluble resin is too great or if the blending amount of the water-soluble resin is too great, then the water-soluble resin is easily entwined (entangled) within the molecule or between the molecules; and in such a case, the dispersion effect of the pigment in the ink is not sufficiently realized. On the other hand, if the molecular weight of the water-soluble resin is too small or if the blending amount of the water-soluble resin is too small, then the above-described effect of pigment aggregation on the paper cannot be obtained.

In view of the effect of the water-soluble resin as described above, the water-soluble resin preferably includes at least one water-soluble resin selected from the group consisting of polyvinylpyrrolidone, polyvinyl alcohol, and poly-N-vinylacetoamide.

For the reason as described above, the weight average molecular weight of the water-soluble resin is, for example, 20,000 to 1,000,000, preferably 25,000 to 800,000, and more preferably 30,000 to 500,000.

In the evaluation method of the present invention, when the pigment ink as the evaluation objective contains the water-soluble resin, for example, then $X=1.5$ is given (a 1.5% by weight aqueous sodium chloride solution is added) in the first aggregation property evaluation, and $Y=2.0$ is given (a 2.0% by weight aqueous sodium chloride solution is added) in the second aggregation property evaluation. On this condition, when the dispersion of the pigment is maintained in the first aggregation property evaluation, the dispersion stability of the pigment when the pigment ink is brought in contact with the dye ink before the printing is judged to be good or satisfactory. Further, when the pigment aggregates in the second aggregation property evaluation, the optical density of the printed matter is judged to be good or satisfactory. Accordingly, it is possible to investigate the blending ratios of the pigment and the water-soluble resin in the pigment ink. In this case, the solid content blending ratio (pigment ratio) of the pigment with respect to the entire pigment ink is preferably 1% by weight to 10% by weight, more preferably 2% by weight to 9% by weight, and much more preferably 3% by weight to 8% by weight. The blending ratio of the water-soluble resin (water-soluble resin ratio) with respect to the entire pigment ink is preferably not more than 0.1% by weight, in view of the effect of the water-soluble resin as described above. The lower limit value of the water-soluble resin ratio is, for example, 0.001% by weight, preferably 0.005% by weight, and more preferably 0.01% by weight, in view of the effect of the water-soluble resin as described above. When the resin, in which the water-soluble resin ratio is not less than 0.001% by weight, is selected, the force, which accelerates the aggregation of the pigment in the ink, is not excessively strengthened. Therefore, the shock aggregation of the pigment is not caused at the mixing stage of mixing the pigment and the resin during the preparation of the ink; and it is possible to stably produce the ink. When the water-soluble resin ratio is not less than 0.001% by weight, it is also easy to control the concentration of the water-soluble resin. Also in this meaning, it is possible to stably produce the ink. In this procedure, by selecting the pigment ink, of which the dispersion stability of the pigment when the pigment ink is brought in contact with the dye ink before the printing is judged to be good in the first aggregation property evaluation and the optical density of the printed matter is judged to be good in the second aggregation property evaluation, it is possible to obtain the pigment ink of which the dispersion stability of the pigment when the pigment ink is brought in contact with the dye ink before the printing is excellent and the optical density of the printed matter is high.

In the evaluation method of the present invention, it is preferable that the water-soluble resin, which is contained in the pigment ink as the evaluation objective, is a nonionic resin. The reason for this is as follows. For example, when an ionic resin such as an acrylic resin is added to the ink, the pigment tends to aggregate extremely easily, because the ion concentration in the ink is increased. For this reason, the possibility is increased that the shock aggregation of the pigment is caused at the mixing stage of mixing the pigment and the resin during the preparation of the ink; and it is feared that the stable production of the ink might be affected thereby. Further, in a case that the aggregation property of the pigment is controlled to be within an objective range of the present invention by adding the ionic resin, it is necessary that the water-soluble resin ratio should be made extremely low, which is not suitable for the stable production of the ink in view of the fact that it is difficult to control the concentration of the water-soluble resin as well.

In the evaluation method of the present invention, the pigment ink as the evaluation objective may contain a water-soluble dye, instead of the water-soluble resin. By containing the water-soluble dye in the pigment ink, it is also possible to accelerate the aggregation of the pigment on the recording medium such as the printing paper sheet and increase the optical density of the printed matter. The effect of the water-soluble dye can be considered as follows. The water-soluble dye exists in the pigment ink accompanied by the counter ion such as sodium ion. On the other hand, the pigment is dispersed owing to the fact that the negatively charged surfaces of the pigment particles repel with each other. However, by the presence of the counter ion which is positively charged, the dispersion of the pigment becomes hard to be maintained, leading to a state that the pigment is easily aggregated. Accordingly, when the pigment ink is landed on the paper surface, the aggregation of the pigment is further accelerated or promoted, and thus a printed matter having sufficient optical density is obtained also due to the color development (coloring) of the dye itself, in addition to the enhancing effect of the optical density brought about by the pigment aggregation.

The water-soluble dye is not limited, and includes, for example, direct dyes, acid dyes, basic dyes, and reactive dyes. Specified examples of the water-soluble dye include, for example, C. I. Direct Black, C. I. Direct Blue, C. I. Direct Red, C. I. Direct Yellow, C. I. Direct Orange, C. I. Direct Violet, C. I. Direct Brown, C. I. Direct Green, C. I. Acid Black, C. I. Acid Blue, C. I. Acid Red, C. I. Acid Yellow, C. I. Acid Orange, C. I. Acid Violet, C. I. Basic Black, C. I. Basic Blue, C. I. Basic Red, C. I. Basic Violet, and C. I. Food Black. C. I. Direct Black includes, for example, C. I. Direct Blacks 17, 19, 32, 51, 71, 108, 146, 154, and 168. C. I. Direct Blue includes, for example, C. I. Direct Blues 6, 22, 25, 71, 86, 90, 106, and 199. C. I. Direct Red includes, for example, C. I. Direct Reds 1, 4, 17, 28, 83, and 227. C. I. Direct Yellow includes, for example, C. I. Direct Yellows 12, 24, 26, 86, 98, 132, and 142. C. I. Direct Orange includes, for example, C. I. Direct Oranges 34, 39, 44, 46, and 60. C. I. Direct Violet includes, for example, C. I. Direct Violets 47 and 48. C. I. Direct Brown includes, for example, C. I. Direct Brown 109. C. I. Direct Green includes, for example, C. I. Direct Green 59. C. I. Acid Black includes, for example, C. I. Acid Blacks 2, 7, 24, 26, 31, 52, 63, 112, and 118. C. I. Acid Blue includes, for example, C. I. Acid Blues 9, 22, 40, 59, 93, 102, 104, 117, 120, 167, 229, and 234. C. I. Acid Red includes, for example, C. I. Acid Reds 1, 6, 32, 37, 51, 52, 80, 85, 87, 92, 94, 115, 180, 256, 289, 315, and 317. C. I. Acid Yellow includes, for example, C. I. Acid Yellows 11, 17, 23, 25, 29, 42, 61, and 71. C. I. Acid Orange includes, for example, C. I. Acid Oranges 7 and 19. C. I. Acid Violet includes, for example, C. I. Acid Violet 49. C. I. Basic Black includes, for example, C. I. Basic Black 2. C. I. Basic Blue includes, for example, C. I. Basic Blues 1, 3, 5, 7, 9, 24, 25, 26, 28, and 29. C. I. Basic Red includes, for example, C. I. Basic Reds 1, 2, 9, 12, 13, 14, and 37. C. I. Basic Violet includes, for example, C. I. Basic Violets 7, 14, and 27. C. I. Food Black includes, for example, C. I. Food Blacks 1 and 2.

The water-soluble dyes as exemplified above are excellent, for example, in the characteristics such as the vividness and the stability. In the evaluation method of the present invention, the pigment ink as the evaluation objective may contain only one type of the water-soluble dye, or the pigment ink may contain two or more types of the water-soluble dyes.

In the evaluation method of the present invention, in a case that the pigment ink as the evaluation objective contains the water-soluble dye, for example, $X=1.0$ is given (a 1.0% by weight aqueous sodium chloride solution is added) in the first aggregation property evaluation, and $Y=2.0$ is given (a 2.0% by weight aqueous sodium chloride solution is added) in the second aggregation property evaluation. On this condition, when the dispersion of the pigment is maintained in the first aggregation property evaluation, the dispersion stability of the pigment when the pigment ink is brought in contact with the dye ink before the printing is judged to be good. When the pigment aggregates in the second aggregation property evaluation, the optical density of the printed matter is judged to be good. Accordingly, it is possible to investigate the blending ratios of the pigment and the water-soluble dye in the pigment ink. In this procedure, the blending ratio (pigment ratio) of the solid content of the pigment with respect to the entire pigment ink is preferably 1% by weight to 10% by weight, more preferably 2% by weight to 9% by weight, and much more preferably 3% by weight to 8% by weight. The blending ratio (dye ratio) of the water-soluble dye with respect to the entire pigment ink is preferably 0.1% by weight to 5% by weight, more preferably 0.25% by weight to 4% by weight, and much more preferably 0.4% by weight to 3% by weight. By selecting the pigment ink, of which the dispersion stability of the pigment when the pigment ink is brought in contact with the dye ink before the printing is judged to be good in the first aggregation property evaluation and the optical density of the printed matter is judged to be good in the second aggregation property evaluation, it is possible to obtain the pigment ink of which the dispersion stability of the pigment when the pigment ink is brought in contact with the dye ink before the printing is excellent and the optical density of the printed matter is high.

In the evaluation method of the present invention, as the means to control the aggregation property of the pigment contained in the ink by adding the ionic substance to the pigment ink as the evaluation objective, it is also possible to conceive a method, in which an organic acid salt or an inorganic salt is added, other than the method in which the water-soluble dye is added into the ink. However, the addition of the organic acid salt or the inorganic salt causes the aggregation of the pigment excessively suddenly. Therefore, the possibility is increased that the shock aggregation of the pigment is caused at the mixing stage of mixing the pigment and the salt during the preparation of the ink; and it is feared that the stable production of the ink might be affected thereby. In a case that the aggregation property of the pigment is controlled to be within an objective range of the present invention by adding the organic acid salt or the inorganic salt, it is necessary that the concentration of the salt should be made extremely low, which is not suitable for the stable production of the ink in view of the fact that it is difficult to control the concentration of the salt as well. In particular, when the organic acid salt is added, then there is a possibility that the organic acid salt might be decomposed in a time-dependent manner, and pH of the ink might be possibly lowered, which is not preferred.

In the evaluation method of the present invention, the pigment ink as the evaluation objective may further contain a conventionally known additive, if necessary. The additive includes, for example, surfactants, viscosity-adjusting agents, surface tension-adjusting agents, and fungicides.

In the evaluation method of the present invention, the pigment ink as the evaluation objective can be prepared, for example, such that the pigment, water, and optionally other additive component(s) are mixed uniformly or homogeneously by any conventionally known method, and undissolved matters are removed by a filter or the like.

Next, the ink jet recording apparatus which performs recording with a pigment ink produced in accordance with the evaluation method of the present invention will be briefly explained. In general, the ink jet recording apparatus includes an ink-accommodating section and an ink-jet head, and discharges inks accommodated in the ink-accommodating section by the ink jet head. In the ink-accommodating section, the pigment ink for ink-jet recording which is produced in accordance with the evaluation method of the present invention or inks which constitute the ink set is/are accommodated.

FIG. 1 shows an exemplary construction of the ink-jet recording apparatus by way of example. As shown in FIG. 1, the ink jet recording apparatus 1 includes, as main constitutive members, four ink cartridges 2, an ink jet head 3, a head unit 4, a carriage 5, a driving unit 6, a platen roller 7, and a purge unit 8.

Each of the four ink cartridges 2 contains each one of the inks of four colors of yellow, magenta, cyan, and black. For example, the black ink is the pigment ink produced in accordance with the evaluation method of the present invention, and the combination of the pigment ink and the yellow, magenta and cyan inks is the ink set produced in accordance with the present invention. The ink-jet head 3 performs the printing on a recording medium P such as the printing paper. The head unit 4 is provided with the ink jet head 3. Nozzles through which the four color inks are jetted are formed in an ink jetting surface (nozzle-formed surface) of the ink-jet head 3. The four ink cartridges 2 and the head unit 4 are provided on the carriage 5. The driving unit 6 reciprocatively moves (reciprocates) the carriage 5 in a linear direction. The platen roller 7 extends in the reciprocating direction of the carriage 5, and the platen roller 7 is arranged to be opposite to or to face the ink-jet head 3.

The driving unit 6 includes a carriage shaft 9, a guide plate 10, two pulleys 11, 12, and an endless belt 13. When the pulley 11 is rotated positively or reversely by the driving of a carriage motor 101, the carriage 5, which is joined to the endless belt 13, is reciprocatively moved in the linear direction along the carriage shaft 9 and the guide plate 10 in accordance with the positive or reverse rotation of the pulley 11.

The recording medium P is fed from a paper feed cassette (not shown) provided at a side portion or a lower portion of the ink-jet recording apparatus 1.

A wiper member 20 is arranged in the purge unit 8 to be adjacent to the purge unit 8, at a position of the purge unit 8 on the side of the platen roller 7. The wiper member 20 is formed to have a spatula-shaped form. The wiper member 20 performs wiping of the nozzle-formed surface of the ink jet head 3, in accordance with the movement of the carriage 5.

Next, an explanation will be given about a production method for producing the pigment ink for ink jet recording and the ink set including the pigment ink for the ink-jet recording, with the use of the evaluation method for the pigment ink for ink-jet recording of the present invention. In the production method of the present invention, a blending ratio of the pigment and the water-soluble resin is determined, by the evaluation method for evaluating the pigment ink for ink-jet recording of the present invention, such that dispersion of the pigment is maintained in the first aggregation property evaluation and that the pigment aggregates in the second aggregation property evaluation; and the pigment and the water-soluble resin are blended in accordance with the blending ratio. In a case of producing an ink set for ink-jet recording including a pigment ink and a dye ink, the pigment ink blended as described above may be combined with the dye ink. The dye ink may includes at least one ink selected from the group consisting of an yellow ink, a magenta ink and a cyan ink; and it is especially preferable that the dye ink includes all of inks of three colors of yellow ink, magenta ink, and cyan ink. When all of the inks of three colors are included, it is possible to realize the adaptation to the full color recording. The dye ink may further include inks of other colors. The dye inks of other colors include, for example, black inks, red inks, green inks, blue inks, and light inks having low dye concentrations (light yellow inks, light magenta inks, light cyan inks, light black inks, light red inks, light green inks, and light blue inks). As the dye ink, it is allowable to use, for example, conventionally known dye inks.

EXAMPLES

Next, Examples of the present invention will be explained. The present invention is neither limited to nor restricted by Examples described below at all.

Example 1

Components except for CAB-O-JET (trade name) 300, which were included in ink composition components (Tables 1 and 2), were mixed uniformly or homogeneously to obtain ink solvents. Subsequently, the ink solvents were added little by little to CAB-O-JET (trade name) 300, followed by being mixed uniformly or homogeneously. After that, obtained mixtures were filtrated through a membrane filter (pore size 3.00 μm) of the cellulose acetate type produced by Toyo Roshi Kaisha, Ltd., and thus pigment inks 1 to 18 for ink-jet recording as evaluation objectives were prepared.

The respective pigment inks were evaluated in accordance with the following methods.
(a) Method for Evaluating Aggregation Property of Pigment
(a-1-1) First Aggregation Property Evaluation 1

10 g of each of the pigment inks was weighed into a beaker. Subsequently, 1 g of a 1.0% by weight aqueous sodium chloride solution was added, while agitating the pigment ink by a magnetic stirrer. After the agitation was continued for about 10 minutes, the pigment ink was observed by a laser microscope, and the evaluation was made in accordance with the following evaluation criterion. In the following evaluation criterion, the phrase "pigment did not aggregate" means that any secondary particle (a cluster of pigment particles), in which the maximum distance (diameter of the cross section) was not less than 1.0 μm in the cross section at which the cross sectional area of one pigment particle becomes maximum, was not observed. The phrase "pigment aggregated" means that the secondary particle, in which the maximum distance was not less than 1.0 μm, was observed. The maximum distance refers to the maximum distance among distances ranging from certain points to the farthest points in the cross section.

Evaluation Criterion for First Aggregation Property Evaluation 1
    G: Pigment did not aggregate.
    NG: Pigment aggregated.

(a-1-2) First Aggregation Property Evaluation 2

10 g of each of the pigment inks was weighed into a beaker. Subsequently, 1 g of a 1.5% by weight aqueous sodium chloride solution was added, while agitating the pigment ink by a magnetic stirrer. After the agitation was continued for about 10 minutes, the pigment ink was observed by a laser microscope, and the evaluation was made in accordance with the following evaluation criterion. The meanings of the terms in the following evaluation criterion are same as or equivalent to those in the first aggregation property evaluation 1 described above.

Evaluation Criterion for First Aggregation Property Evaluation 2
    G: Pigment did not aggregate.
    NG: Pigment aggregated.

(a-2-1) Second Aggregation Property Evaluation 1

10 g of each of the pigment inks was weighed into a beaker. Subsequently, 1 g of a 2.5% by weight aqueous sodium chloride solution was added, while agitating the pigment ink by a magnetic stirrer. After the agitation was continued for about 10 minutes, the pigment ink was observed by a laser microscope, and the evaluation was made in accordance with the following evaluation criterion. The meanings of the terms in the following evaluation criterion are same as or equivalent to those in the first aggregation property evaluation 1 described above.

Evaluation Criterion for Second Aggregation Property Evaluation 1
    G: Pigment aggregated.
    NG: Pigment did not aggregate.

(a-2-2) Second Aggregation Property Evaluation 2

10 g of each of the pigment inks was weighed into a beaker. Subsequently, 1 g of a 2.0% by weight aqueous sodium chloride solution was added, while agitating the pigment ink by a magnetic stirrer. After the agitation was continued for about 10 minutes, the pigment ink was observed by a laser microscope, and the evaluation was made in accordance with the following evaluation criterion. The meanings of the terms in the following evaluation criterion are same as or equivalent to those in the first aggregation property evaluation 1 described above.

Evaluation Criterion for Second Aggregation Property Evaluation 2
    G: Pigment aggregated.
    NG: Pigment did not aggregate.

Subsequently, various physical properties and characteristics of the respective pigment inks were measured or evaluated in accordance with the following methods.

(b) Optical Density (OD) Value

An evaluation sample was prepared by performing the printing at a resolution of 600 dpi×600 dpi (amount of one liquid droplet: about 19 pL) on a regular paper sheet (Laser Print produced by Hammermill) by using a digital multifunction machine DCP-330C provided with an ink-jet printer produced by Brother Industries, Ltd. The optical density (OD) value of the evaluation sample was measured by using a spectrophotometric colorimetry meter Spectrolino (light source: $D_{50}$, field: 2°, ANSI T) produced by Gretag Macbeth, and the evaluation was made in accordance with the following evaluation criterion.

Evaluation Criterion for Optical Density (OD) Value
    A: OD value was not less than 1.3.
    B: OD value was not less than 1.2 and less than 1.3.
    C: OD value was less than 1.2.

(c-1) Contact Test 1 with Dye Ink 20 g of each of the pigment inks was weighed into a beaker. Subsequently, 1 g of a magenta ink (dye ink), which had been charged to an ink cartridge LC10M produced by Brother Industries, Ltd., was added while agitating the pigment ink by a magnetic stirrer. After the agitation was continued for about 10 minutes, the pigment ink was observed by a laser microscope, and the evaluation was made in accordance with the following evaluation criterion. The meanings of the terms in the following evaluation criterion are same as or equivalent to those in the first aggregation property evaluation 1 described above.

Evaluation Criterion for Contact Test 1 with Dye Ink
    G: Pigment did not aggregate.
    NG: Pigment aggregated.

(c-2) Contact Test 2 with Dye Ink 20 g of each of the pigment inks was weighed into a beaker. Subsequently, 1 g of a yellow ink (dye ink), which had been charged to an ink cartridge LC10Y produced by Brother Industries, Ltd., was added while agitating the pigment ink by a magnetic stirrer. After the agitation was continued for about 10 minutes, the pigment ink was observed by a laser microscope, and the evaluation was made in accordance with the following evaluation criterion. The meanings of the terms in the following evaluation criterion are same as or equivalent to those in the first aggregation property evaluation 1 described above.

Evaluation Criterion for Contact Test 2 with Dye Ink
    G: Pigment did not aggregate.
    NG: Pigment aggregated.

Compositions and evaluation results of the pigment inks 1 to 5 are shown in Table 1. Further, compositions and evaluation results of the pigment inks 6 to 18 are shown in Table 2. In Tables 1 and 2, Mw represents the weight average molecular weight. In Tables 1 and 2, the K-value of polyvinylpyrrolidone is the viscosity characteristic value which correlates with the weight average molecular weight. The relationship between the K-value and the weight average molecular weight is as follows.

| K-value | Weight average molecular weight |
| --- | --- |
| 90 | ~360,000 |
| 30 | ~40,000 |
| 15 | ~10,000 |

TABLE 1

|  |  | Pigment ink 1 | Pigment ink 2 | Pigment ink 3 | Pigment ink 4 | Pigment ink 5 |
|---|---|---|---|---|---|---|
| Ink composition (% by weight) | CAB-O-JET (trade name) 300 (*1) | 33.0 (4.95) | 33.0 (4.95) | 33.0 (4.95) | 33.0 (4.95) | 33.0 (4.95) |
|  | GE191-205 (*2) | 0.05 (0.01) | — | — | — | — |
|  | Polyvinyl alcohol Mw = 85,000-124,000 | — | 0.015 | — | — | — |
|  | Polyvinyl alcohol Mw = 31,000-50,000 | — | — | 0.03 | — | — |
|  | Polyvinyl pyrrolidone K value 90 | — | — | — | 0.01 | — |
|  | Polyvinyl pyrrolidone K value 30 | — | — | — | — | 0.03 |
|  | Glycerol | 23.0 | 25.0 | 27.0 | 24.5 | 26.5 |
|  | Dipropylene glycol propyl ether | 2.0 | 2.0 | 2.0 | 2.0 | 2.0 |
|  | Water | balance | balance | balance | balance | balance |
| Evaluation | First aggregation property evaluation 1 | G | G | G | G | G |
|  | First aggregation property evaluation 2 | G | G | G | G | G |
|  | Second aggregation property evaluation 1 | G | G | G | G | G |
|  | Second aggregation property evaluation 2 | G | G | G | G | G |
| Physical property & characteristic | Optical density (OD) value | A | A | A | A | A |
|  | Contact test 1 with dye ink | G | G | G | G | G |
|  | Contact test 2 with dye ink | G | G | G | G | G |

(*1): Self-dispersible black pigment, produced by Cabot Specialty Chemicals, pigment solid content: 15% by weight (parenthesized numerals indicate pigment solid content amounts).
(*2): Poly-N-vinylacetoamide, produced by Showa Denko K. K., active ingredient: 20% by weight (parenthesized numerals indicate active ingredient amounts).

TABLE 2

|  |  | Pigment ink 6 | Pigment ink 7 | Pigment ink 8 | Pigment ink 9 | Pigment ink 10 |
|---|---|---|---|---|---|---|
| Ink composition (% by weight) | CAB-O-JET (trade name) 300 (*1) | 33.0 (4.95) | 33.0 (4.95) | 33.0 (4.95) | 33.0 (4.95) | 33.0 (4.95) |
|  | GE191-205 (*2) | — | 0.01 (0.002) | 0.5 (0.1) | — | — |
|  | Polyvinyl alcohol Mw = 85,000-124,000 | — | — | — | 0.005 | 0.03 |
|  | Polyvinyl alcohol Mw = 31,000-50,000 | — | — | — | — | — |
|  | Polyvinyl alcohol Mw = 13,000-23,000 | — | — | — | — | — |
|  | Polyvinyl pyrrolidone K value 90 | — | — | — | — | — |
|  | Polyvinyl pyrrolidone K value 30 | — | — | — | — | — |
|  | Polyvinyl pyrrolidone K value 15 | — | — | — | — | — |
|  | Glycerol | 29.5 | 25.0 | 20.0 | 27.0 | 25.0 |
|  | Dipropylene glycol propyl ether | 2.0 | 2.0 | 2.0 | 2.0 | 2.0 |
|  | Water | balance | balance | balance | balance | balance |
| Evaluation | First aggregation property evaluation 1 | G | G | — | G | — |
|  | First aggregation property evaluation 2 | G | G | NG | G | NG |
|  | Second aggregation property evaluation 1 | NG | — | G | — | G |
|  | Second aggregation property evaluation 2 | NG | NG | G | NG | G |
| Physical property & characteristic | Optical density (OD) value | B | B | A | B | A |
|  | Contact test 1 with dye ink | G | G | NG | G | NG |
|  | Contact test 2 with dye ink | G | G | NG | G | NG |

|  |  | Pigment ink 11 | Pigment ink 12 | Pigment ink 13 | Pigment ink 14 | Pigment ink 15 |
|---|---|---|---|---|---|---|
| Ink composition (% by weight) | CAB-O-JET (trade name) 300 (*1) | 33.0 (4.95) | 33.0 (4.95) | 33.0 (4.95) | 33.0 (4.95) | 33.0 (4.95) |
|  | GE191-205 (*2) | — | — | — | — | — |
|  | Polyvinyl alcohol Mw = 85,000-124,000 | — | — | — | — | — |
|  | Polyvinyl alcohol Mw = 31,000-50,000 | 0.015 | 0.10 | — | — | — |
|  | Polyvinyl alcohol Mw = 13,000-23,000 | — | — | 1.0 | — | — |
|  | Polyvinyl pyrrolidone K value 90 | — | — | — | 0.003 | 0.10 |
|  | Polyvinyl pyrrolidone K value 30 | — | — | — | — | — |
|  | Polyvinyl pyrrolidone K value 15 | — | — | — | — | — |
|  | Glycerol | 28.0 | 24.5 | 28.0 | 27.5 | 26.5 |
|  | Dipropylene glycol propyl ether | 2.0 | 2.0 | 2.0 | 2.0 | 2.0 |
|  | Water | balance | balance | balance | balance | balance |
| Evaluation | First aggregation property evaluation 1 | G | — | G | G | — |
|  | First aggregation property evaluation 2 | G | NG | G | G | NG |
|  | Second aggregation property evaluation 1 | — | G | — | — | G |
|  | Second aggregation property evaluation 2 | NG | G | NG | NG | G |
| Physical property & characteristic | Optical density (OD) value | B | A | C | B | A |
|  | Contact test 1 with dye ink | G | NG | G | G | NG |
|  | Contact test 2 with dye ink | G | NG | G | G | NG |

TABLE 2-continued

|  |  | Pigment ink | | |
|---|---|---|---|---|
|  |  | 16 | 17 | 18 |
| Ink composition (% by weight) | CAB-O-JET (trade name) 300 (*1) | 33.0 (4.95) | 33.0 (4.95) | 33.0 (4.95) |
|  | GE191-205 (*2) | — | — | — |
|  | Polyvinyl alcohol Mw = 85,000-124,000 | — | — | — |
|  | Polyvinyl alcohol Mw = 31,000-50,000 | — | — | — |
|  | Polyvinyl alcohol Mw = 13,000-23,000 | — | — | — |
|  | Polyvinyl pyrrolidone K value 90 | — | — | — |
|  | Polyvinyl pyrrolidone K value 30 | 0.005 | 0.05 | — |
|  | Polyvinyl pyrrolidone K value 15 | — | — | 1.0 |
|  | Glycerol | 28.0 | 25.5 | 27.5 |
|  | Dipropylene glycol propyl ether | 2.0 | 2.0 | 2.0 |
|  | Water | balance | balance | balance |
| Evaluation | First aggregation property evaluation 1 | G | — | G |
|  | First aggregation property evaluation 2 | G | NG | G |
|  | Second aggregation property evaluation 1 | G | G | — |
|  | Second aggregation property evaluation 2 | NG | G | NG |
| Physical property & characteristic | Optical density (OD) value | B | A | C |
|  | Contact test 1 with dye ink | G | NG | G |
|  | Contact test 2 with dye ink | G | NG | G |

(*1): Self-dispersible black pigment, produced by Cabot Specialty, pigment solid content: 15% by weight (parenthesized numerals indicate pigment solid content amounts).
(*2): Poly-N-vinylacetoamide, produced by Showa Denko K. K., active ingredient: 20% by weight (parenthesized numerals indicate active ingredient amounts).

As shown in Table 1, the results of both of the optical density (OD) values and the contact test with the dye ink were good for the pigment inks 1 to 5 in which both of the results of the first aggregation property evaluation 2 and the second aggregation property evaluation 2 were "G". On the other hand, as shown in Table 2, the optical density (OD) values were low for the pigment ink 6 which did not contain the water-soluble resin and in which the result of the second aggregation property evaluation 2 was "NG" and for the pigment inks 7, 9, 11, 14, and 16 which had the small water-soluble resin ratios and in which the results of the second aggregation property evaluation 2 were "NG". The results of the contact test with the dye ink were inferior for the pigment inks 8, 10, 12, 15, and 17 which had the large water-soluble resin ratios and in which the results of the first aggregation property evaluation 2 were "NG". Further, the optical density (OD) values were extremely low for the pigment inks 13 and 18 which contained the water-soluble resins having the low weight average molecular weights and in which the results of the second aggregation property evaluation 2 were "NG". According to the results as described above, the pigment inks 1 to 5 were judged to be such pigment inks that the optical density of the printed matter was high and the dispersion stability of the pigment when the pigment ink was brought in contact with the dye ink before the printing was excellent.

From the results shown in Tables 1 and 2, the followings are appreciated. From the results of the pigment inks 1-7, 9, 11, 13, 14, 16 and 18, in a case that the pigment did not aggregate in the first aggregation property evaluation 1 (using 1.0% by weight aqueous sodium chloride solution) and the first aggregation property evaluation 2 (using 1.5% by weight aqueous sodium chloride solution), then the dispersion stability of the pigment when the pigment ink is brought in contact with the dye ink is satisfactory. Further, from the results of the pigment inks 1-5, 8, 10, 12, 15 and 17, in a case that the pigment aggregated in the second aggregation property evaluation 1 (using 2.5% by weight aqueous sodium chloride solution) and the second aggregation property evaluation 2 (using 2.0% by weight aqueous sodium chloride solution), then the optical density (OD) value is satisfactory. Accordingly, it can be said that the first aggregation property evaluation 1 and the first aggregation property evaluation 2 reflect the dispersion stability of the pigment when the pigment ink is brought in contact with the dye ink; and that the second aggregation property evaluation 1 and the second aggregation property evaluation 2 reflect the optical density (OD) value. Therefore, in order to know the dispersion stability of the pigment when the pigment ink is brought into contact with the dye ink, it is allowable to perform at least one of the first aggregation property evaluations 1 and 2, rather than actually performing the contact test of the pigment and dye inks as described above. Further, in order to know the optical density (OD) value of the printed item printed by using the pigment ink, it is allowable to perform at least one of the second aggregation property evaluations 1 and 2, rather than actually performing the measurement of the optical density as described above.

As explained above, the first aggregation property evaluations 1 and 2 reflect the dispersion stability of the pigment ink when the pigment ink is brought in contact with the dye ink. However, in a case of seeking a pigment ink in which the dispersion stability of the pigment is higher, it is allowable to perform only the first aggregation property evaluation 2, while omitting the first aggregation property evaluation 1.

Table 3 shows evaluation results and water-soluble resin ratios of the pigment ink 6 which did not contain the water-soluble resin and the pigment inks 16, 5, and 17 which used polyvinylpyrrolidone having the K value of 30 as the water-soluble resin, among the pigment inks 1 to 18.

TABLE 3

|  | Pigment ink | | | |
|---|---|---|---|---|
|  | 6 | 16 | 5 | 17 |
| Water-soluble resin ratio (% by weight) | 0 | 0.005 | 0.03 | 0.05 |
| First aggregation property evaluation 2 | G | G | G | NG |
| Second aggregation property evaluation 2 | NG | NG | G | G |
| Optical density (OD) value | B (1.23) | B (1.28) | A (1.31) | A (1.33) |
| Contact test 1 with dye ink | G | G | G | NG |
| Contact test 2 with dye ink | G | G | G | NG |

As shown in Table 3, the results of the second aggregation property evaluation 2 were NG and the optical density (OD) values were low for the pigment ink 6 which had the water-soluble resin ratio of 0% by weight and for the pigment ink 16 which had the water-soluble resin ratio of 0.005% by weight. Further, the result of the first aggregation property evaluation 2 was NG and the result of the contact test with the dye ink was inferior for the pigment ink 17 which had the water-soluble resin ratio of 0.05% by weight. On the other hand, both of the results of the first aggregation property evaluation 2 and the second aggregation property evaluation 2 were G and the results of both of the optical density (OD) value and the contact test with the dye ink were good for the pigment ink 5 which had the water-soluble resin ratio of 0.03% by weight. In this way, according to this embodiment, the water-soluble resin ratio was successfully derived with ease in order to obtain the pigment ink in which the optical density of the printed matter was high and the dispersion stability of the pigment when the pigment ink was brought in contact with the dye ink before the printing was excellent. The explanation has been made above as exemplified by the case in which polyvinyl pyrrolidone having the K value of 30 is used as the water-soluble resin. However, even when any water-soluble resin other than the above was used, the preferred water-soluble resin ratio was successfully derived with ease in the same manner as described above.

Example 2

Components except for CAB-O-JET (trade name) 300, which were included in ink composition components (Tables 4 and 5), were mixed uniformly or homogeneously to obtain ink solvents. Subsequently, the ink solvents were added little by little to CAB-O-JET (trade name) 300, followed by being mixed uniformly or homogeneously. After that, obtained mixtures were filtrated through a membrane filter (pore size 3.00 μm) of the cellulose acetate type produced by Toyo Roshi Kaisha, Ltd., and thus pigment inks 19 to 34 for ink-jet recording as evaluation objectives were prepared.

The respective pigment inks were evaluated in accordance with the following methods.
(a) Method for Evaluating Aggregation Property of Pigment
(a-1) First Aggregation Property Evaluation 1

10 g of each of the pigment inks was weighed into a beaker. Subsequently, 1 g of a 1.0% by weight aqueous sodium chloride solution was added, while agitating the pigment ink by a magnetic stirrer. After the agitation was continued for about 10 minutes, the pigment ink was observed by a laser microscope, and the evaluation was made in accordance with the following evaluation criterion. The meanings of the terms in the following evaluation criterion are same as or equivalent to those in the first aggregation property evaluation 1 of Example 1. Note that in this example, the first aggregation property evaluation 2, which was performed in Example 1, was not performed because only the minimum dispersion stability of the pigment was considered.
Evaluation Criterion for First Aggregation Property Evaluation 1

G: Pigment did not aggregate.

NG: Pigment aggregated.

(a-2-1) Second Aggregation Property Evaluation 1

10 g of each of the pigment inks was weighed into a beaker. Subsequently, 1 g of a 2.5% by weight aqueous sodium chloride solution was added, while agitating the pigment ink by a magnetic stirrer. After the agitation was continued for about 10 minutes, the pigment ink was observed by a laser microscope, and the evaluation was made in accordance with the following evaluation criterion. The meanings of the terms in the following evaluation criterion are same as or equivalent to those in the first aggregation property evaluation 1 of Example 1.
Evaluation Criterion for Second Aggregation Property Evaluation 1

G: Pigment aggregated.

NG: Pigment did not aggregate.

(a-2-2) Second Aggregation Property Evaluation 2

10 g of each of the pigment inks was weighed into a beaker. Subsequently, 1 g of a 2.0% by weight aqueous sodium chloride solution was added, while agitating the pigment ink by a magnetic stirrer. After the agitation was continued for about 10 minutes, the pigment ink was observed by a laser microscope, and the evaluation was made in accordance with the following evaluation criterion. The meanings of the terms in the following evaluation criterion are same as or equivalent to those in the first aggregation property evaluation 1 of Example 1.
Evaluation Criterion for Second Aggregation Property Evaluation 2

G: Pigment aggregated.

NG: Pigment did not aggregate.

Subsequently, various physical properties and characteristics of the respective pigment inks were measured or evaluated in accordance with the following methods.
(b) Optical Density (OD) Value An evaluation sample was prepared by performing the printing at a resolution of 600 dpi×300 dpi (amount of one liquid droplet: about 19 pL) on a regular paper sheet (Laser Print produced by Hammer Mill) by using a digital multifunction machine DCP-330C provided with an ink jet printer produced by Brother Industries, Ltd. The optical density (OD) value of the evaluation sample was measured by using a spectrophotometric colorimetry meter Spectrolino (light source: $D_{50}$, field: 2°, ANSI T) produced by Gretag Macbeth, and the evaluation was made in accordance with the following evaluation criterion.

Evaluation Criterion for Optical Density (OD) Value

A: OD value was not less than 1.25.

B: OD value was not less than 1.2 and less than 1.25.

C: OD value was less than 1.2.

(c-1) Contact Test 1 with Dye Ink 10 g of each of the pigment inks was weighed into a beaker. Subsequently, 1 g of a magenta ink (dye ink), which had been charged to an ink cartridge LC10M produced by Brother Industries, Ltd., was added while agitating the pigment ink by a magnetic stirrer. After the agitation was continued for about 10 minutes, the pigment ink was observed by a laser microscope, and the evaluation was made in accordance with the following evaluation criterion. The meanings of the terms in the following evaluation criterion are same as or equivalent to those in the first aggregation property evaluation 1 of Example 1.
Evaluation Criterion for Contact Test 1 with Dye Ink G: Pigment did not aggregate.

NG: Pigment aggregated.

(c-2) Contact Test 2 with Dye Ink 10 g of each of the pigment inks was weighed into a beaker. Subsequently, 1 g of a yellow ink (dye ink), which had been charged to an ink cartridge LC10Y produced by Brother Industries, Ltd., was added while agitating the pigment ink by a magnetic stirrer. After the agitation was continued for about 10 minutes, the pigment ink was observed by a laser microscope, and the evaluation was made in accordance with the following evaluation criterion. The meanings of the terms in the following evaluation criterion are same as or equivalent to those in the first aggregation property evaluation 1 of Example 1.

Evaluation Criterion for Contact Test 2 with Dye Ink
G: Pigment did not aggregate.
NG: Pigment aggregated.

Compositions and evaluation results of the pigment inks 19 to 23 are shown in Table 4. Further, compositions and evaluation results of the pigment inks 24 to 34 are shown in Table 5.

TABLE 4

|  |  | Pigment ink | | | | |
|---|---|---|---|---|---|---|
|  |  | 19 | 20 | 21 | 22 | 23 |
| Ink composition (% by weight) | CAB-O-JET (trade name) 300 (*1) | 40.00 (6.00) | 40.00 (6.00) | 40.00 (6.00) | 40.00 (6.00) | 40.00 (6.00) |
|  | C.I. Food Black 1 (*2) | 0.50 | — | — | — | — |
|  | C.I. Food Black 2 (*2) | — | 0.75 | — | — | — |
|  | C.I. Direct Black 19 | — | — | 1.00 | — | — |
|  | C.I. Direct Black 22 | — | — | — | 1.00 | — |
|  | WATER BLUE 3 (*3) | — | — | — | — | 0.75 |
|  | Glycerol | 17.00 | 17.00 | 17.00 | 17.00 | 17.00 |
|  | Dipropylene glycol propyl ether | 2.30 | 2.30 | 2.30 | 2.30 | 2.30 |
|  | Water | balance | balance | balance | balance | balance |
| Evaluation | First aggregation property evaluation 1 | G | G | G | G | G |
|  | Second aggregation property evaluation 1 | G | G | G | G | G |
|  | Second aggregation property evaluation 2 | G | G | G | G | G |
| Physical property & characteristic | Optical density (OD) value | A | A | A | A | A |
|  | Contact test 1 with dye ink | G | G | G | G | G |
|  | Contact test 2 with dye ink | G | G | G | G | G |

(*1): Self-dispersible black pigment, produced by Cabot Specialty Chemicals, pigment solid content: 15% by weight (parenthesized numerals indicate pigment solid content amounts).
(*2): Produced by Daiwa Kasei Co., Ltd.
(*3): Produced by Orient Chemical Industries, Ltd.

TABLE 5

|  |  | Pigment ink | | | |
|---|---|---|---|---|---|
|  |  | 24 | 25 | 26 | 27 |
| Ink composition (% by weight) | CAB-O-JET (trade name) 300 (*1) | 40.00 (6.00) | 40.00 (6.00) | 40.00 (6.00) | 40.00 (6.00) |
|  | C.I. Food Black 1 (*2) | — | 0.25 | 1.00 | — |
|  | C.I. Food Black 2 (*2) | — | — | — | 0.25 |
|  | C.I. Direct Black 19 | — | — | — | — |
|  | C.I. Direct Black 22 | — | — | — | — |
|  | WATER BLUE 3 (*3) | — | — | — | — |
|  | Glycerol | 17.00 | 17.00 | 17.00 | 17.00 |
|  | Dipropylene glycol propyl ether | 2.30 | 2.30 | 2.30 | 2.30 |
|  | Water | balance | balance | balance | balance |
| Evaluation | First aggregation property evaluation 1 | G | G | NG | G |
|  | Second aggregation property evaluation 1 | NG | — | — | G |
|  | Second aggregation property evaluation 2 | NG | NG | G | NG |
| Physical property & characteristic | Optical density (OD) value | C | C | A | B |
|  | Contact test 1 with dye ink | G | G | NG | G |
|  | Contact test 2 with dye ink | G | G | NG | G |

|  |  | Pigment ink | | | |
|---|---|---|---|---|---|
|  |  | 28 | 29 | 30 | 31 |
| Ink composition (% by weight) | CAB-O-JET (trade name) 300 (*1) | 40.00 (6.00) | 40.00 (6.00) | 40.00 (6.00) | 40.00 (6.00) |
|  | C.I. Food Black 1 (*2) | — | — | — | — |
|  | C.I. Food Black 2 (*2) | 1.25 | — | — | — |
|  | C.I. Direct Black 19 | — | 0.75 | 1.25 | — |
|  | C.I. Direct Black 22 | — | — | — | 0.75 |
|  | WATER BLUE 3 (*3) | — | — | — | — |
|  | Glycerol | 17.00 | 17.00 | 17.00 | 17.00 |
|  | Dipropylene glycol propyl ether | 2.30 | 2.30 | 2.30 | 2.30 |
|  | Water | balance | balance | balance | balance |
| Evaluation | First aggregation property evaluation 1 | NG | G | NG | G |
|  | Second aggregation property evaluation 1 | — | — | — | — |
|  | Second aggregation property evaluation 2 | G | NG | G | NG |

TABLE 5-continued

| Physical property & characteristic | Optical density (OD) value | A | B | A | C |
|---|---|---|---|---|---|
| | Contact test 1 with dye ink | NG | G | NG | G |
| | Contact test 2 with dye ink | NG | G | NG | G |

| | | Pigment ink | | |
|---|---|---|---|---|
| | | 32 | 33 | 34 |
| Ink composition (% by weight) | CAB-O-JET (trade name) 300 (*1) | 40.00 (6.00) | 40.00 (6.00) | 40.00 (6.00) |
| | C.I. Food Black 1 (*2) | — | — | — |
| | C.I. Food Black 2 (*2) | — | — | — |
| | C.I. Direct Black 19 | — | — | — |
| | C.I. Direct Black 22 | 1.25 | — | — |
| | WATER BLUE 3 (*3) | — | 0.50 | 1.25 |
| | Glycerol | 17.00 | 17.00 | 17.00 |
| | Dipropylene glycol propyl ether | 2.30 | 2.30 | 2.30 |
| | Water | balance | balance | balance |
| Evaluation | First aggregation property evaluation 1 | NG | G | NG |
| | Second aggregation property evaluation 1 | — | — | — |
| | Second aggregation property evaluation 2 | G | NG | G |
| Physical property & characteristic | Optical density (OD) value | A | C | A |
| | Contact test 1 with dye ink | NG | G | NG |
| | Contact test 2 with dye ink | NG | G | NG |

(*1): Self-dispersible black pigment, produced by Cabot Specialty Chemicals, pigment solid content: 15% by weight (parenthesized numerals indicate pigment solid content amounts).
(*2): Produced by Daiwa Kasei Co., Ltd.
(*3): Produced by Orient Chemical Industries, Ltd.

As shown in Table 4, the results of both of the optical density (OD) values and the contact test with the dye ink were good for the pigment inks 19 to 23 in which both of the results of the first aggregation property evaluation 1 and the second aggregation property evaluation 2 were "G". On the other hand, as shown in Table 5, the optical density (OD) values were low for the pigment ink 24 which did not contain the water-soluble dye and for the pigment inks 25, 27, 29, 31, and 33 which had the small water-soluble dye ratios. The results of the contact test with the dye ink were inferior for the pigment inks 26, 28, 30, 32, and 34 which had the large water-soluble dye ratios and in which the results of the first aggregation property evaluation 1 were "NG". According to the results as described above, the pigment inks 19 to 23 were judged to be such pigment inks that the optical density of the printed matter was high and the dispersion stability of the pigment when the pigment ink was brought in contact with the dye ink before the printing was excellent.

From the results shown in Tables 4 and 5, the followings are appreciated. From the results of the pigment inks 19-25, 27, 29, 31 and 33, in a case that the pigment did not aggregate in the first aggregation property evaluation 1 (using 1.0% by weight aqueous sodium chloride solution), then the dispersion stability of the pigment when the pigment ink is brought in contact with the dye ink is satisfactory. Further, from the results of the pigment inks 19-23, 26, 28, 30, 32 and 34, in a case that the pigment aggregated in the second aggregation property evaluation 1 (using 2.5% by weight aqueous sodium chloride solution) and the second aggregation property evaluation 2 (using 2.0% by weight aqueous sodium chloride solution), then the optical density (OD) value is satisfactory. Accordingly, it can be said that the first aggregation property evaluation 1 reflects the dispersion stability of the pigment when the pigment ink is brought in contact with the dye ink; and that the second aggregation property evaluation 1 and the second aggregation property evaluation 2 reflect the optical density (OD) value. Therefore, in order to know the dispersion stability of the pigment when the pigment ink is brought into contact with the dye ink, it is allowable to perform the first aggregation property evaluation 1, rather than actually performing the contact test of the pigment and dye inks as described above. Further, in order to know the optical density (OD) value of the printed item printed by using the pigment ink, it is allowable to perform at least one of the second aggregation property evaluations 1 and 2, rather than actually performing the measurement of the optical density as described above.

Table 6 shows evaluation results and water-soluble dye ratios of the pigment ink 24 which did not contain the water-soluble dye and the pigment inks 27, 20, and 28 which used C. I. Food Black 2 as the water-soluble dye, among the pigment inks 19 to 34.

TABLE 6

| | Pigment ink | | | |
|---|---|---|---|---|
| | 24 | 27 | 20 | 28 |
| Water-soluble dye ratio (% by weight) | 0 | 0.25 | 0.75 | 1.25 |
| First aggregation property evaluation | G | G | G | NG |
| Second aggregation property evaluation 2 | NG | NG | G | G |
| Optical density (OD) value | C (1.17) | B (1.20) | A (1.26) | A (1.30) |
| Contact test 1 with dye ink | G | G | G | NG |
| Contact test 2 with dye ink | G | G | G | NG |

As shown in Table 6, the results of the second aggregation property evaluation 2 were NG and the optical density (OD) values were low for the pigment ink 24 which had the water-soluble dye ratio of 0% by weight and for the pigment ink 27 which had the water-soluble dye ratio of 0.25% by weight. Further, the result of the first aggregation property evaluation 1 was NG and the result of the contact test with the dye ink was inferior for the pigment ink 28 which had the water-soluble dye ratio of 1.25% by weight. On the other hand, both of the results of the first aggregation property evaluation 1 and the second aggregation property evaluation 2 were "G" and the results of both of the optical density (OD) value and the contact test with the dye ink were good for the pigment ink 20 which had the water-soluble dye ratio of 0.75% by weight. In this way, according to this embodiment, the water-soluble dye ratio was successfully derived with ease in order to obtain the pigment ink in which the optical density of the printed matter was high and the dispersion stability of the pigment when the pigment ink was brought in contact with the dye ink before the printing was excellent. The explanation has been made above as exemplified by the case in which C. I. Food Black 2 is used as the water-soluble dye. However, even when any water-soluble dye other than the above was used, the preferred water-soluble dye ratio was successfully derived with ease in the same manner as described above.

From the above results, it is appreciate that, with respect to a general ratio of the water-soluble dye with which both the results of the optical density (OD) value and the contact test with the dye ink are satisfactory, is generally preferably 0.5% by weight to 1.0% by weight and in particular 0.5% by weight to 0.75% by weight. However, depending on the water-soluble dyes, for example with respect to C.I. Direct Black 19 and 22, the optical density (OD) value was low even though the ratio of the water-soluble dye was within the above range. Therefore, the inventors paid attention to the effect of the water-soluble dye in the pigment ink and calculated the concentration of the counter ion possessed by the water-soluble dye, and attempted whether or not it was possible to generalize both the results of the optical density (OD) value and the contact test with the dye ink with the concentration of such counter ion. However, the inventors found out that although both the results of the optical density (OD) value and the contact test with the dye were satisfactory when the concentration of the counter ion was 0.053% by weight to 0.084% by weight, this did not apply to all of the pigment inks. The inventors consider, as the reason for this, that there might be some effect by the molecular structure of the water-soluble dye, etc. However, from the results of the examples, it is appreciated and the attention should be paid to the fact that regardless of the kind and/or the amount of the water-soluble dye, the pigment ink which is capable of preventing the clog-up of the nozzle that would be otherwise caused due to the contact of the pigment ink and the dye ink before the printing and which is excellent in the optical density after the printing, can be correctly and easily evaluated only by performing the first aggregation property evaluation and the second aggregation property evaluation.

By evaluating the pigment ink with the first and second aggregation property evaluations in accordance with the examples, it is possible to obtain the pigment ink which is capable of preventing the clog-up of the nozzle that would be otherwise caused due to the contact of the pigment ink and the dye ink before the printing and which is excellent in the optical density after the printing. Further, by using the composition of the pigment ink thus obtained can be used to produce or mass-produce the pigment ink. The production process of the pigment ink according to the present invention will be explained briefly with reference to a flow chart shown in FIG. 2. First, the pigment ink is prepared with a predetermined composition (S10). The first aggregation property evaluation is performed for the prepared pigment ink, as in Example 1 or 2 (S12). The concentration of the sodium chloride used in the first aggregation property evaluation may be changed depending on a case that the pigment ink contains the water-soluble resin or a case that the pigment ink contains water-soluble dye. Furthermore, it is allowable to perform the two kinds of evaluation, namely the first aggregation property evaluation 1 and the first aggregation property evaluation 2 as in Example 1, or it is allowable to perform only the first aggregation property evaluation 1 as in Example 2. If the first aggregation property evaluation is satisfied, then the process is proceeded to the second aggregation property evaluation (S14); and if the first aggregation property evaluation is not satisfied, the process is returned to Step S10 and the composition of the pigment ink is prepared again. In the second aggregation property evaluation, the second aggregation property evaluation is performed for the pigment ink as in Example 1 or 2. With respect to the second aggregation property evaluation, it is allowable to perform both of the second aggregation property evaluations 1 and 2, or it is allowable to perform only one of the second aggregation property evaluations 1 and 2. Then, the pigment ink, which satisfies the second aggregation property evaluation, is considered as a suitable pigment ink (S16), and it is possible to mass-produce a pigment ink having the same composition as that of the suitable pigment ink. On the other hand, if the second aggregation property evaluation is not satisfied, the process is returned to Step S10, and the composition of the pigment ink is prepared again. In the flow chart shown in FIG. 2, the first aggregation property evaluation is performed first. However, it is allowable to perform the second aggregation property evaluation first instead of the first aggregation property evaluation; or it is allowable to perform both the first and second aggregation property evaluations in parallel. In the production process, it is also allowable that at first a plurality of pigment inks having various compositions are prepared (S10), and that a pigment ink(s), among the plurality of pigment inks, which satisfies both the first aggregation property evaluation (S12) and the second aggregation property evaluation (S14) is selected.

By combining the pigment ink produced as described above with a dye ink, it is possible to produce an ink set.

As described above, according to the evaluation method for evaluating the pigment ink for ink-jet recording of the present invention, it is possible to easily evaluate both of the optical density of the printed matter and the dispersion stability of the pigment when the pigment ink is brought in contact with the dye ink before the printing. The evaluation method for evaluating the pigment ink for ink-jet recording of the present invention is widely applicable to the evaluation of various pigment inks for ink-jet recording. Therefore, by using the evaluation method, it is possible to produce the pigment ink which is capable of preventing the clog-up of the nozzle and which is excellent in the optical density and to produce the ink set including the pigment ink together with the dye ink.

What is claimed is:
1. An evaluation method for evaluating a pigment ink for ink jet recording which is used together with a dye ink for ink jet recording and which contains a pigment and water, the method comprising:
performing an aggregation property evaluation method for the pigment in which 10 parts by weight of an aqueous sodium chloride solution is added to 100 parts by weight of the pigment ink, the aggregation property evaluation method for the pigment including:
performing first aggregation property evaluation in which the aqueous sodium chloride solution having an X % by weight concentration is added to the pigment ink; and
performing second aggregation property evaluation in which the aqueous sodium chloride solution having a Y % by weight concentration is added to the pigment ink;
wherein the concentrations of the aqueous sodium chloride solutions are set to fulfill a following condition (A) in the first aggregation property evaluation and the second aggregation property evaluation:

$1.0 \leq X < Y \leq 2.5$ (A).

2. The evaluation method according to claim 1, wherein X=1.0 is given in the first aggregation property evaluation, and Y=2.5 is given in the second aggregation property evaluation.

3. The evaluation method according to claim 1, wherein the pigment ink for ink jet recording further contains a water-soluble resin; X=1.5 is given in the first aggregation property evaluation; and Y=2.0 is given in the second aggregation property evaluation.

4. The evaluation method according to claim 3, wherein the water-soluble resin is selected from the group consisting of polyvinylpyrrolidone, polyvinyl alcohol, and poly-N-vinylacetoamide.

5. The evaluation method according to claim 1, wherein the pigment ink for ink-jet recording further contains a water-soluble dye; X=1.0 is given in the first aggregation property evaluation; and Y=2.0 is given in the second aggregation property evaluation.

6. The evaluation method according to claim 1, wherein a dispersion state of the pigment is evaluated in the first aggregation property evaluation when the pigment ink for ink-jet recording is brought in contact with the dye ink for ink-jet recording before printing; and
an optical density of a printed matter is evaluated in the second aggregation property evaluation.

7. The evaluation method according to claim 1, wherein dispersion stability of the pigment, when the pigment ink for ink jet recording is brought in contact with the dye ink for ink jet recording before printing, is judged to be good if dispersion of the pigment is maintained in the first aggregation property evaluation; and
an optical density of a printed matter is judged to be good if the pigment aggregates in the second aggregation property evaluation.

8. The evaluation method according to claim 1, wherein the first aggregation property evaluation includes a first aggregation property evaluation 1 in which the aqueous sodium chloride solution having a 1.0% by weight concentration is added, and a first aggregation property evaluation 2 in which the aqueous sodium chloride solution having a 1.5% by weight concentration is added.

9. The evaluation method according to claim 1, wherein the second aggregation property evaluation includes a second aggregation property evaluation 1 in which the aqueous sodium chloride solution having a 2.5% by weight concentration is added, and a second aggregation property evaluation 2 in which the aqueous sodium chloride solution having a 2.0% by weight concentration is added.

10. A production method for producing a pigment ink for ink jet recording, the method comprising:
preparing a pigment ink having a predetermined composition containing a pigment and water;
performing the first aggregation property evaluation and the second aggregation property evaluation for the pigment ink with the evaluation method as defined in claim 1;
preparing the pigment ink with the predetermined composition if dispersion of the pigment is maintained in the first aggregation property evaluation and if the pigment aggregates in the second aggregation property evaluation.

11. A method for producing an ink set for ink-jet recording, comprising:
preparing a pigment ink in accordance with the production method as defined in claim 10; and
combining the prepared pigment ink and a dye ink.

12. An evaluation method for evaluating a pigment ink for ink jet recording which is used together with a dye ink for ink jet recording, the method comprising:
preparing pigment inks of various compositions, each of the pigment inks containing a pigment and water;
performing a first aggregation property evaluation, for evaluating aggregation property of the pigment for each of the pigment inks, in which 10 parts by weight of a 1.0 to 1.5% by weight aqueous sodium chloride solution is added to 100 parts by weight of the pigment ink; and
performing a second aggregation property evaluation, for evaluating the aggregation property of the pigment for each of the pigment inks, in which 10 parts by weight of a 2.0 to 2.5% by weight aqueous sodium chloride solution is added to 100 parts by weight of the pigment ink; and
selecting a pigment ink, among the pigment inks of various compositions, in which the pigment does not aggregate in the first aggregation property evaluation and the pigment aggregates in the second aggregation property evaluation.

13. The evaluation method according to claim 12, wherein each of the pigment inks of various compositions further contains a water-soluble resin; and
a 1.5% by weight aqueous sodium chloride solution is used in the first aggregation property evaluation and a 2.0% by weight aqueous sodium chloride solution is used in the second aggregation property evaluation.

14. The evaluation method according to claim 13, wherein the water-soluble resin is selected from the group consisting of polyvinylpyrrolidone, polyvinyl alcohol, and poly-N-vinylacetoamide.

15. The evaluation method according to claim 12, wherein each of the pigment inks of various compositions further contains a water-soluble dye; and
a 1.0% by weight aqueous sodium chloride solution is used in the first aggregation property evaluation and a 2.0% by weight aqueous sodium chloride solution is used in the second aggregation property evaluation.

* * * * *